United States Patent [19]

Rubin

[11] Patent Number: 5,340,803
[45] Date of Patent: Aug. 23, 1994

[54] METHOD AND COMPOSITIONS FOR TREATING TUMORS HAVING HIGH TYROSINASE ACTIVITY

[75] Inventor: David Rubin, San Diego, Calif.

[73] Assignee: Co Enzyme Technology Ltd., San Diego, Calif.

[21] Appl. No.: 57,666

[22] Filed: May 5, 1993

Related U.S. Application Data

[63] Continuation-in-part of Ser. No. 787,347, Nov. 4, 1991, abandoned.

[51] Int. Cl.$^5$ .................... A01N 43/04; A61K 31/70; C07G 3/00; C07H 15/00
[52] U.S. Cl. .................... 514/25; 536/4.1; 536/17.9; 536/53
[58] Field of Search .............. 514/25; 536/4.1, 17.9, 536/53

[56] References Cited

U.S. PATENT DOCUMENTS

| | | | |
|---|---|---|---|
| 4,337,760 | 7/1982 | Rubin | 604/52 |
| 4,424,348 | 1/1984 | Rubin | 536/17.9 |
| 4,481,195 | 11/1984 | Rubin | 536/4.1 |
| 4,812,590 | 3/1989 | Saari | 560/137 |

OTHER PUBLICATIONS

Res. Comm. in Chem. Path. and Pharm. 41(3):441–454 (1983).
Br. J. Cancer 54:693–698 (1986).
Pigment Cell Research 2:421–426 (1989).
Eur. J. Med. Chem. 16(5):461–464 (1981).
Eur. J. Med. Chem. 22:393–402 (1987).
Biochem. J. 245:537–542 (1987).
Hydroxyanisole IRL Press Ltd., Oxford, England 153–164.
Clinical Ocology 7:227–234 (1981).
Biochemical Phamacology 23:3173–3177 (1974).

*Primary Examiner*—Nathan M. Nutter
*Attorney, Agent, or Firm*—Browdy and Neimark

[57] ABSTRACT

Tumor cells which have β-glucuronidase and tyrosinase activity are selectively treated by administration of a conjugate of a cytotoxic compound which is a substrate for tyrosinase and glucuronic acid or a pharmaceutically acceptable salt or ester thereof particularly the methyl-triacetylated form of glucuronic acid. Among the cytotoxic phenolic compounds which are substrates for tyrosinase which can be used are 4-hydroxyanisole, butylated hydroxyanisole, L-3,4-dihydroxy-phenylalanine, dopamine (3,4-dihydroxyphenethylamine), terbutylcatechol, hydroquinone, resorcinol, 6-hydroxydopa (3,4,6-trihydeoxyphenylalanine) and methyl gallate.

The efficacy of the treatment is enhanced by also administering a compound that inhibits the action of glutathione reductase.

27 Claims, No Drawings

METHOD AND COMPOSITIONS FOR TREATING TUMORS HAVING HIGH TYROSINASE ACTIVITY

CROSS REFERENCES TO RELATED APPLICATIONS

This application is a continuation-in-part of Ser. No. 07/787,347, filed Nov. 4, 1991, now abandoned, and PCT/US92/09473, filed Nov. 4, 1992, the entire contents of both of which are hereby incorporated by reference.

FIELD OF THE INVENTION

The present invention is directed to methods and compositions for treating tumors and other metastatic diseases exhibiting high tyrosinase and $\beta$-glucuronidase activity. The invention is further directed to methods and compositions for treating tumors having high tyrosinase and $\beta$-glucuronidase activity in which the toxicity of the materials used to treat the tumors is localized at the site of the tumors.

There have been many reports in the prior art relating to the general concept of providing direct transport of an agent which is toxic to tumor cells directly to tumors having $\beta$-glucuronidase activity by conjugating the agent with glucuronic acid. Among such reports are Von Ardenne, M. et al., *Acressologie*, 1976, 176 (5): 261–264; East German Patent No. 122,386; German Offenlegungsschrift 22 12 014; Sweeney et al., *Cancer Research* 31: 477–478, 1971; Baba et al., Gann, 69: 283–284; and Ball, *Biochem. Pharm.* 23: 3171–3177 (1974).

Von Ardenne suggest broadly many types of aglycones which may be conjugated to glucuronic acid and will be active at the tumor site. There include, broadly, alkylating groups, antimetabolites, cytotoxins, membrane-active (lyric) groups, glycolysis stimulators, respiration inhibitors, inorganic and organic acids and cell cycle stoppers. The East German patent also suggests many such combinations, including 5-fluorouracil-glucuronide, aniline mustard-glucuronide and many others. The Offenlegungsschrift also mentions a large number of glucuronides. Sweeney et al. disclose the anti-tumor activity of mycophenolic acid-$\beta$-D-glucuronides. Baba et al. note the anti-tumor activity of 5-fluorouracil-o-$\beta$-D-glucuronide, and Ball discloses the anti-tumor activity of p-hydroxyaniline mustard glucuronide.

Kneen in European Patent Application 054,924, discloses phenyl ether compounds which can be used to make tumors more sensitive to radio therapy.

Rubin, in U.S. Pat. Nos. 4,337,760 and 4,481,195, discloses methods for treating tumors having high $\beta$-glucuronidase activity with glucuronides with aglycones toxic to the tumor cells with great safety toward the rest of the body by first administering an alkalinizing agent in an amount sufficient to maintain the pH level of non-tumor tissues at approximately 7.4 during the glucuronide treatment to inactivate $\beta$-glucuronidase activity in the rest of the body. Thus, the toxic agent is directed only to the cancer cells, as opposed to all of the healthy cells of the body, since the aglycone is only released at the cancer site. Tumors having high glucuronidase activity can be identified by assaying tumor cells obtained in a biopsy for $\beta$-glucuronidase activity, or by administering a glucuronide whose aglycone has been labelled with a radioactive isotope. If upon a full body scan it is found that the radioisotope is accumulated at any specific areas of the body, this will indicate not only the location of the tumor but the fact that the tumor has sufficient $\beta$-glucuronidase activity to deconjugate the glucuronide.

The rationale for the use of 4-hydroxyanisole in the treatment of melanoma is based upon the premise that the only cells in vertebrates that contain tyrosinase are the melanocytes. 4-Hydroxyanisole inhibits DNA synthesis, but by itself shows little toxicity. However, it is oxidized by tyrosinase to highly cytotoxic products, and consequently is preferentially toxic to those melanoma cells that contain the enzyme tyrosinase [Riley, *Philos. Trans. R. Soc.* (*Biol.*) 311: 679, 1985].

Morgan et al., in *Clinical Oncology* 7:227–231, 1981, also note that 4-hydroxyanisole, which is oxidized by tyrosinase, gives rise to cytotoxic oxidation products. The specific maelanocytotoxic action of this agent is of particular interest because of its use in treatment of malignant melanoma. It was found that localized malignant melanomas treated by intra-arterial infusion of 4-hydroxyanisole underwent regression, although intravenous administration of the drug was not therapeutically effective. The need to use the intra-arterial route of administration imposes certain limits on the use of 4-hydroxyanisole, since it is not always possible to perfuse the site occupied by a tumor. However, it is believed that, as an adjunct to the conventional treatment of primary melanoma in accessible sites, 4-hydroxyanisole infusion will reduce the dissemination of metastases.

Kanclerz et al., *Br. J. Cancer* 54: 693–698, 1986, reported that animal studies on experimental melanomas have given variable results with respect to the therapeutic efficacy of phenolic depigmentation agents. The most active melanocytotoxic agent was found to be an analog of tyrosine, 4-hydroxyanisole. However, evidence for an antitumor effect of 4-hydroxyanisole on melanoma in vivo was found to be variable and not conclusive.

Unfortunately, intra-arterial infusion of 4-hydroxyanisole has serious clinical drawbacks, including difficulties in placing and maintaining the potency of intra-arterial catheters. Clogging and/or clothing frequently occur, and, furthermore, 4-hydroxyanisole has a short half-life in blood (only nine minutes) after intra-arterial injection.

Saari, in U.S. Pat. No. 4,812,590, discloses that certain carbamates of 4-hydroxyanisole are suitable substitutes for 4-hydroxyanisole in the treatment of melanoma. These carbamates can be delivered by, for example, intravenous injection, and provide increased levels of 4-hydroxyanisole at the tumor site. The delivery of 4-hydroxyanisole is more convenient and safer than many other methods of delivering 4-hydroxyanisole, although, because serum tyrosinase levels may be elevated in patients having tumors with high tyrosinase activity, the metabolic products of 4-hydroxy anisole may be present in locations other than the tumor site.

Pavel et al., *Pigment Cells Research* 2:421–246, 1989, reported an investigation of the human metabolism of 4-hydroxyanisole using urine samples from melanoma patients treated with 4-hydroxyanisole. The most important metabolite of 4-hydroxyanisole was found to be 3,4-dihydroxyanisole, although other metabolic products included 3-hydroxy-4-methxylanisole and 4-hydroxy-3-methoxyanisole, as well as quinone. These compounds were excreted predominantly as sulfates and glucuronides. Unfortunately, when tyrosinase oxidizes 4-hydroxyanisole in the body, the product, 4-methoxybenzoquinone, is extremely toxic. Because the 4-hydroxyanisole is not confined to the tumor site, and because the serum levels of tyrosinase of patients suffering from tyrosinase-active tumors tends to be elevated, there is always the danger in administering 4-hydroxyanisole to such patients that an excess of metabolic products of 4-hydroxyanisole will be present in the blood, and thus exert a cytotoxic effect on cells other than tumor cells.

Chen et al discovered that serum tyrosinase activity in many persons with metastatic diseases was found to be significantly higher than activity in normal persons. Although the highest serum tyrosinase activity was observed in melanoma and breast carcinoma, there is measurable tyrosinase activity in a variety of other metastatic diseases, including lung carcinoma, colon carcinoma, testicular carcinoma, hepatic carcinoma, pancreatic carcinoma, ovarian carcinoma, leukemia, bronchogenic carcinoma, prostate carcinoma, Hodgkin's disease, and rectal carcinoma, the tyrosinase activity of the foregoing diseases listed in decreasing order. In addition, serum melanin bands were demonstrated by polyacrylamide disc gel electrophoresis of serum tyrosinase followed by incubation of the gel with L-dopa at room temperature overnight to form melanin bands. The following types of metastatic disease demonstrated serum melanins bands with this technique: mouth carcinoma, multiple myeloma, carcinoma of the stomach, carcinoma of the larynx, carcinoma of the cervix, carcinoma of the tonsil, lymphoma, lymphosarcoma, thyroid carcinoma, carcinoma of cecum, endometrial carcinoma, polycythemia, thymoma, lymphadenopathy, and vertebral carcinoma.

Although the elevation of serum tyrosinase level is explicable in some diseases such as melanoma and breast carcinoma, the high tyrosinase content in melanoma and breast skin increases the tyrosinase circulation level in the blood. Although it has not yet been determined if malignant disease causes a high yield of serum tyrosinase or if a high yield of serum tyrosinase causes malignant disease, it has been postulated that serum immunoglobulins are involved as tyrosinase carriers. Whatever the involvement of tyrosinase in metastatic diseases, there is an elevated level of serum tyrosinase in the case of a great many metastatic diseases.

Passi et al., in *Biochem. J.* 245: 536–542, 1987, compared the cytotoxicity of a number of phenols in vitro. These researches found that in vitro, two melanotic human melanoma cell lines IRE 1 and IRE 2, and the lymphoma- and leukemia-derived cell lines Raji and K 562, and noted that there was no significant differences in percentage survival among the different cell lines for each drug tested. The major component of toxicity up to 24 hours of di- and tri-phenols was due to toxic oxygen species aching outside the cells, and not to cellular uptake of these phenols per se. It is believed that scavenger enzymes may interfere with the cytotoxic effect of some of these phenols. Additionally, it was noted that the cytotoxic effect of these phenols was not necessarily related to their being substrates for tyrosinase, as the level of toxicity of butylated hydroxyanisole, which is not a substrate of tyrosinase, was significantly higher than that of 4-hydroxyanisole, which is a substrate of tyrosinase.

With respect to dosages of 4-hydroxyanisole to be given Wallevik et al. report in "Non-specific Inhibition of In Vitro Growth of Human Melanoma Cells, Fibroblasts, and Carcinoma cells by 4-Hydroxyanisole" in Hydroxyanisole: Recent Adv. Anti-Melanoma Ther., pp. 153–164 (1984) Editor, Patrick A. Riley, that 4-hydroxyanisole was inhibitory to cultures of human melanotic and amelanotic melanoma cell lines, human fibroblasts and a human bladder carcinoma at concentrations of $10^{-3}$M to $10^{-5}$M. This activity was independent of tyrosinase activity, as high tyrosinase activity was only connected with the melanotic cell line. Unfortunately, the therapeutic concentration of 4-hydroxyanisole is difficult to obtain in tissue by intra-arterial infusion of the drug. Furthermore, infusion is given only for one hour twice a day, which is an exposure of the cells that in vitro has no inhibitory effect, even at a high concentration of 4-hydroxyanisole.

It has also been found that a genetic aberration in chromosomes 7 and 13 of certain malignant growths expresses itself in a vast biosynthesis of two specific enzymes: $\beta$-glucuronidase and tyrosinase. Among these malignant growths are breast cancer, lung cancer, colon cancer, melanoma and gastric cancer.

Para-methoxy-phenyl glucuronide damages cancer cells by excessive production of hydrogen peroxide. Hydrogen peroxide oxidizes many amino acid side chains, such as methionine, by transferring one of the oxygen atoms from the hydrogen peroxide to an acceptor molecule, resulting in damage to the cells. However, cancer cells as well as other living cells contain reduced glutathione (GSH). Glutathione, a tripeptide made up of glutamic acid, cysteine, and glycine, in its reduced state as GSH, can react with hydrogen peroxide to mitigate the oxidative damage to cell membranes, as shown in the following equation:

Tyrosinase is known to convert several phenols, such as its natural substrate, tyrosine, to catechols and quinones. These compounds react strongly with SH-groups, and are highly toxic to normal cells. Therefore, it is essential that the cytotoxic phenols such as 4-hydroxyanisole be delivered efficiently to the tumor cells, and only to the tumor cells, and that the reaction product of tyrosinase on the substrate, such as 4-hydroxyanisole, be retained in the tumor cells.

SUMMARY OF THE INVENTION

It is an object of the present invention to overcome the aforementioned deficiencies in the prior art.

It is another object of the present invention to provide a method and composition for treating metastatic cells.

It is another object of the present invention to provide a composition and method for treating metastatic cells without damaging normal cells.

It is a further object of the present invention to provide a two-step method for treating tumors whereby healthy cells are spared from treatment.

It is a further object of the present invention to provide a method for treating tumor cells using a three-step process wherein healthy cells are spared from treatment.

According to the present invention, a cytotoxic phenol which is a substrate for tyrosinase is conjugated to a glucuronide to provide a compound for treating tumors which have β-glucuronidase activity and tyrosinase activity. The glucuronide, upon contact with the β-glucuronidase, is cleaved to produce the tyrosinase substrate cytotoxic phenol at the tumor site, which, upon being acted upon by tyrosinase, then can exert its cytotoxic effect on the tumor cells. In this manner, the truly toxic compound is delivered only to the tumor cells, and there is virtually no contact with the healthy cells, since the cytotoxic phenol is not released at the tumor site until the glucuronide compound has been cleaved by the β-glucuronidase at the tumor site. This avoids contact of healthy cells with the cytotoxic phenol, and the reaction products of the cytotoxic phenol and any tyrosinase can be limited to the tumor site.

The cytotoxic phenolic compounds which are substrates for tyrosinase compounds which can be used in the present invention are those which have been found to be toxic to tumor cells, including tyrosine, 4-hydroxyanisole, butylated hydroxyanisole, L-3,4-dihydroxyphenylalanine, dopamine (3,4-dihydroxyphenethylamine), terbutylcatechol, hydroquinone, resorcinol, 6-hydroxydope (3,4,6-trihydeoxyphenylalanine), 4-tert-butyl phenol, 4-tert-amyl phenol and 4-benomethoxy phenol and methyl gallate. These compounds are conjugated to glucuronic acid by any convenient means to form the compounds of the present invention.

In addition, the cytotoxic phenolic compounds conjugated to glucuronic acid can be used in the acetylated form. That is, when the conjugates are formed by conjugating a phenolic compound with methyl(tri-O-acetyl-α-D-glucopyranosyl bromide)-uronate, a triacetyl methyl ester is formed. This triacetyl methyl ester can be used in the acetylated form. Since these acetyl groups are not easily removed, the compounds are not particularly cytotoxic to normal cells. However, since primitive cells, such as growing cancer cells, can produce many different types of enzymes, including acetylase, these primitive cells can readily remove the acetyl groups on the acetylated conjugates to provide active forms of the compound directly at the site of a growing tumor. Of particular importance are the 3-acetylated conjugates, since the 3-acetylated conjugates are lipid soluble and are retained by the body at the tumor site for a much longer period of time than the unacetylated conjugates. The 3-acetylated conjugates have also been found able to cross the blood-brain barrier.

Of the conjugates of the present invention, the glucuronide of 4-hydroxy-anisole (or PMPG, for para-methoxy-phenyl glucuronide) is a preferred compound. Because this compound is a glucuronide, it possess a low toxicity, as an important mechanisms of the liver is to detoxify toxins via conjugation with glucuronic acid.

Para-methoxy-phenyl glucuronide has the following formula:

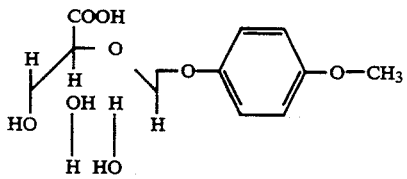

In another embodiment of the present invention, the prodrug is para-methoxy-phenyl glucuronide which is hydrolyzed at the cancer site by beta-glucuronidase to yield 4-hydroxy anisole (para-methoxy phenol). The 4-hydroxy anisole then becomes a susbtrate for the enzyme tyrosinase, which oxidizes the 4-hydroxy anisole to methoxy ortho benzoquinone. The methoxy ortho benzoquinone is an unstable molecule that spontaneously release hydrogen peroxide. This released hydrogen peroxide damages the cell membranes. The inhibition of glutathione reductase by a quinine compound further enhances the oxidative damage in the cancerous cells.

A number of methods can be used to manufacture the glucuronic acid conjugates according to the present invention, including those disclosed in Rubin, U.S. Pat. No. 4,481,195 and Rubin, U.S. Pat. No. 4,424,348, the entire contents of both of which are incorporated by reference.

The cytotoxic phenols are conjugated to glucuronic acid by conjugation of the phenol with methyl(tri-O-acetyl-α-D-glucopyranosyl bromide)-uronate, which is the active form of glucuronic acid, and may be produced in accordance with the teachings of Bollenback, et al., J. Am. Chem. Soc. 77: 3310, 1955.

The cytotoxic phenol is introduced to the methyl(tri-O-acetyl-β-D-glucopyranosyl)bromide uronate in a solution of phenol catalyzed by a small catalytic amount of silver oxide. Besides phenol, there may be used, as solvent, quinoline, methyl nitrile or methyl cyanide. Silver carbonate may also be used as the catalyst.

Another method of condensation is to use sodium or potassium hydroxide as the condensing agent in aqueous acetone solution. A stoichiometric excess of cytotoxic phenol is preferably used. The reaction solution is maintained at room temperature for 24 hours or until the reaction to form the triacetyl methyl ester is complete.

The triacetyl methyl ester can be used as such or can be converted to the acid form of the conjugate by reaction of the triacetyl methyl ester as obtained above with a ½ molar amount of 0.5N barium hydroxide which is added slowly to this solution to form a white precipitate. Preferably, an excess of barium hydroxide is added until there is no more precipitation.

The addition of 0.5N sulfuric acid, volume to volume, followed by cooling in ice water for 20 minutes, releases the free glucuronides.

The mixture is then filtered, and the supernatant is dried in vacuum and crystallized from ether.

The triacetylated form of the glucuronide is the preferred form of the compounds to be used in accordance with the present invention. However, the free acid form of the conjugates may also be used when a water-soluble form of the conjugate is desired. Therefore, whenever the term "glucuronide compound" is used in the present specification and claims, it is understood to include not only the free glucuronic acid form of the conjugate but also acetylated glucuronic acid conjugates as well as pharmaceutically acceptable salts and esters thereof as discussed hereinabove.

The selectivity of glucuronide compounds toward tumors can be greatly increased and the possible deconjugation of the toxic aglycones in healthy parts of the body can be greatly minimized by administering to the patient, prior to or simultaneously with administration of the glucuronide, an alkalinizing agent which will maintain the pH of the rest of the body at a pH of about 7.4. It is known that the activity of β-glucuronidase activity is substantially nil at a pH of about 7.4. Thus, the administration of alkalinizing agents such as bicarbonates or other basic salts will substantially decrease and eliminate β-glucuronidase activity which occurs naturally in certain healthy tissues such as the kidneys, spleen and liver. Such an administration of alkalinizing agent will not diminish the acidity of the tumor cells themselves, however, in view of the naturally low pH of the tumor cells, the mechanism of prior hyperacidification and the lack of substantial blood perfusion through the tumor area, as well as other possible mechanisms° It has been suggested in the literature, in fact, that bicarbonate will actually increase the acidity of the cancer cells, cf.. Gullino et al., *J.N.C.I.* 34 (6): 857–869, 1965.

Since the β-glucuronidase activity of the tumor cells is enhanced by acidification, and the β-glucuronidase activity of the rest of the body, particularly of the kidneys, will be substantially eliminated by alkalinization, the cytotoxic phenols will only be released at the tumor site itself due to deconjugation of the glucuronides by the action of β glucuronidase. Without the alkalinization step, substantial amounts of toxic materials may be released, for example in the kidneys, and the cytotoxic phenols so released may cause substantial damage to these organs if there is any tyrosinase present at this site. Thus, only through the use of the present invention can glucuronides of phenols which are toxic to tumor cells be used with a great degree of safety and efficacy. The greater the toxicity of the phenols after action of tyrosinase, the more important is the alkalinization step.

Other steps for increasing β-glucuronidase activity at the tumor cells may also be undertaken. One method of accomplishing this is to elevate the temperature of the toxic cells at the time of treatment. This may be done by elevating the temperature of the entire body such as by use of a pyrogenic drug or by elevating the temperatures solely in the area of the toxic cells, such as by microwave radiation or electrical current. Raising of the temperature increases β-glucuronidase activity, thereby increasing the efficiency of the deconjugation of the glucuronides. It is known that, in the temperature range of about 35° to 45° C., an elevation of temperature of 3° C. increases β-glucuronidase activity by 50%.

Known pyrogenic drugs include etiocholanolone, progesterone, dinitrophenol, dinitrocresol, and the like. Because dinitrophenol and dinitrocresol are also cytotoxic, the use of these compounds are preferred, particularly when they are administered as the glucuronide. This gives the result that, when the glucuronide is deconjugated at the tumor site, the aglycone will act not only to denature the cytoplasmic protein, but also to raise the temperatures directly in the region of the tumor cells, thus greatly increasing the efficiency of further deconjugation.

Local hyperthermia in the region of suspected tumor cells is preferred to general hyperthermia, because general hyperthermia will also increase the β-glucuronidase activity in healthy cells. However, because of the alkalinization step, this is not a major problem. If the hyperthermia is local, then this provides an additional degree of certainty that the glucuronides will only become deconjugated at the tumor site. The application of microwave treatment directed at the suspected tumor site is one way to achieve total hyperthermia. Due to the different electrical resistance of tumor cells, another method of achieving some degree of local hyperthermia is by administering a low electrical current through the body.

A further manner of increasing β-glucuronidase activity selectively at tumor cells is by administration of estrogen to female patients or testosterone to male patients, for tumors which are not estrogen- or testosterone-dependent. It has been reported that these compounds induce β-glucuronidase activity in trophoblastic cells. Since certain tumor cells are known to be trophoblastic, this method is particularly useful for those types of cells. The alkalinization step would prevent damage to healthy trophoblastic cells.

Before treatment of patients in accordance with the present invention, it should be ascertained that the particular type of tumor involved has both a high β-glucuronidase activity as well as a high tyrosinase activity. This may be done in a number of ways. One way is to assay tumor cells obtained in a biopsy for β-glucuronidase activity. If such a test is positive, then the pharmaceutical compositions of the present invention may be administered.

A second method is the administration of a glucuronide whose aglycone has been labelled with a radioactive isotope. If, upon a full body scan, it is found that the radioisotope is accumulated at any specific areas of the body, then this will indicate not only the location of the tumor but the fact that the tumor has sufficient β-glucuronidase activity to deconjugate the glucuronide. After this has been determined, the appropriate amount of the glucuronide of choice may be administered. If there are no tumors present, or if the tumors are of the type which do not have β-glucuronidase activity, then there will be no accumulation of radioisotope in the body as the alkalinization step of the present invention eliminates all β-glucuronidase activity and the isotope will be passed through the body.

Another method of diagnosing tumors which are treatable by means of the present invention is to test for the presence of free glucuronic acid in the urine. While the presence of glucuronides in the urine is common, the presence of free glucuronic acid in the urine, and particularly the presence of increasing amounts of glucuronic acid when tested over a period of several days, is a potent indication of the presence of tumors with β-glucuronidase activity. It is hypothesized that the presence of free glucuronic acid in the urine in cancer patients is caused by the action of β-glucuronidase in the cancer cells on the intercellular filaments and connective tissue. Glucuronic acid is a reaction product of such activity because the intercellular filaments and connective tissues are composed of polymers of which glucuronic acid is an element and which are known substrates for the enzyme β-glucuronidase.

A method for distinguishing free glucuronic acid from conjugated glucuronides in the urine has previously been disclosed in Rubin, U.S. Pat. No. 4,337,760. Both glucuronides and glucuronic acid give a chromogenic complex with tetraborate in concentrated sulfuric acid which reacts with m-hydroxydiphenyl to create a colored water-soluble complex. When lead acetate is added at an alkaline pH, the glucuronides precipitate and the addition of ditizone (dithiosemicarbazone) makes a stable complex with the excess lead. Accordingly, an optical reading may be taken representative of the amounts of total glucuronides and free glucuronic acid after tetraborate and m-hydroxydiphenyl have been added. A second reading may then be taken after the conjugated glucuronides and excess lead have been removed from the aqueous phase by the addition of basic lead acetate and after ditizone has been added. Alternatively, the conjugated glucuronides can be removed by reaction with barium hydroxide. The addition of barium hydroxide to the urine sample will cause precipitation of the conjugated glucuronides but not of the free glucuronic acid. After centrifugation and filtration the conjugated glucuronides are eliminated and what remains is only the free glucuronic acid. A reading representative of the amount of free glucuronic acid many then be taken. The alternative procedure bypasses the necessity of the use of ditrizone.

In the urine test for glucuronidase activity, normal patients exhibit between 200 and 400 mg per 24 hours of free glucuronic acid in the urine. Cancer patients with well developed tumors which have β-glucuronidase activity show greater than 200 to 7000 mg per 24 hours of free glucuronic acid. Accordingly, using this above test, if more than about 400 mg per 24 hours of free glucuronide is exhibited, this is an excellent indication of the presence of tumors having a high β-glucuronidase activity.

A negative indication on this urine test will not conclusively rule out the presence of tumors having β-glucuronidase activity, because tumors in their initial stages, although they might have β-glucuronidase activity, might not release sufficient free glucuronic acid to cause a positive reading of the urine. Therefore, the urine test should be repeated, and if an increasing amount of free glucuronic acid is found, then this is another indication of the presence of a tumor having β-glucuronidase activity.

Although 4-hydroxyanisole and other cytotoxic phenols may not generally be toxic to healthy cells, when these substances are substrates to tyrosinase, they are converted to toxic metabolite which have their dominant effect inside the cells, where they are produced (i.e., melanoma cells and melanocytes), as tyrosinase is known to convert several phenols (e.g., its natural substrate, tyrosine) to catechols and quinones which react strongly with SH groups.

Tyrosinase activity of tumor cells can be determined by assaying a sample obtained from a biopsy by the method of Pomerantz, *J. Biol. Chem.* 241: 161, 1966, using L-[3.5-$^3$H]-tyrosine (Amersham TRK 200). Using this method, Wallevik et al. (op. cit.) determined that melanotic melanoma had the greatest tyrosinase activity, while bladder carcinoma and amelanotic melanoma had less but measurable tyrosinase activity. Skin fibroblasts were found to have no tyrosinase activity.

Once it has been determined that the patient has a tumor having both tyrosinase and β-glucuronidase activity, the first step of the treatment is to administer a dose of glucose as, for example, 100 g of honey, glucose, or other simple sugar. Approximately one hour later, an intravenous drip is begun of a solution in distilled water containing approximately 10% glucose and 60 milliequivalents sodium bicarbonate. Approximately 1 liter is administered, assuming no contraindications, and the pH of the urine is checked to determine that it has reached a pH of approximately 7.4. This will establish that the system has become alkalinized and it is now safe to administer the glucuronide. Another liter of the same glucose-bicarbonate solution, but also including the desired amount of glucuronide, is then administered. This is repeated daily as needed. It is desirable to maintain high levels of glucose in the blood during treatment according to the present invention. At least 180% of normal glucose levels is desirable; above 250% is preferable.

If there are contraindications for the administration of bicarbonate, then an antacid may be orally administered. This antacid may be any conventional antacid such as sodium bicarbonate, magnesium bicarbonate, aluminum hydroxide, aluminum magnesium silicate, magnesium carbonate, magnesium hydroxide, magnesium oxide, or the like. The important criterion is that the pH of the urine become approximately 7.4 and remain so during treatment.

The hyperacidification of the tumor cells is caused by a hyperglycemic condition in the patient. Therefore, any hyperglycemic agent may be used as the hyperacidification agent, as, for example, fructose, galactose, lactose or glucagon. Furthermore, it should be understood that this hyperglycemic condition may be effected in any known manner. For example, if the patient is diabetic, then the condition can be brought about by decreasing the insulin administration.

Any agent which will raise the pH of the urine to approximately 7.4 can be used as the alkalinizing agent, including sodium or potassium bicarbonate or citrate, or other basic salts or antacids. While it is preferred that these agents be administered intravenously, they may be administered orally.

When the term "approximately 7.4" is used in the present specification and claims, with respect to the pH level to be maintained in the rest of the body, it should be understood that a pH level slightly above or below 7.4 may be used, although this is not preferred. As the pH deceases from 7.4, the β-glucuronidase activity increases until the optimal pH is reached. Furthermore, below pH 7.0 the rest of the body will not be alkaline but will be acid. Above 7.4 the danger of alkalosis increases without any substantial further decrease in β-glucuronidase activity. A pH level of 7.4 is preferred, as this is physiological pH and cannot be harmful to the body, and it is known that the β-glucuronidase activity in healthy organs is substantially nil at this pH level.

The dosage of the compounds administered should be monitored to avoid any side effects due to the massive release of toxins caused by the dying cancer cells. It may be preferable to treat the patient with the compounds of the present invention in short courses of several days, leaving several days in between to allow any toxins released by the dying cancer cells to leave the body before continuing with treatment.

Besides intravenous administration, the acid form of the glucuronide conjugates may be administered by any means of parenteral administration. However, the free acid form of the glucuronides should not be administered orally, as it is known that β-glucuronidase is present in the digestive tract. The tri-acetylated conjugates, however, can be administered orally, as the β-glucuronidase in the digestive tract does not affect the acetylated conjugates.

The amount of glucuronide conjugate to be administered to any given patient must be determined empirically and will differ depending upon the condition of the patient. Relatively small amounts of the conjugates can be administered at first, with steadily increasing dosages if no adverse effects are noted. Of course, the maximum safe toxicity dosage as determined in routine animal toxicity tests should ever be exceeded.

Optimally, the concentration of glucuronide conjugates to be administered may be sufficient to administer a concentration of from about $5 \times 10^{-4}$M to about $5 \times 10^{-6}$M of the phenolic cytotoxic compound to the tumor site.

It is clear that any tumor cells having both β-glucuronidase activity and tyrosinase activity may be treatable in accordance with the present invention, with the remaining organs of the body being protected by the alkalinization step. Tumors which are known to have β-glucuronidase activity include solid breast tumors and their metastases, bronchogenic carcinoma and its metastases, and lymphomas, as well as lung carcinoma, colon carcinoma, testicular carcinoma, hepatic carcinoma, pancreatic carcinoma, ovarian carcinoma, leukemia, bronchogenic carcinoma, prostate carcinoma, Hodgkin's disease, and rectal carcinoma. Tumors which have high tyrosinase activity, as noted above, include melanoma, amelanotic melanoma, and breast carcinoma, and bladder carcinoma, as well as a number of others noted above.

It is also known that neoplasms which do not have high β-glucuronidase activity, and therefore cannot be treated in accordance with the present invention, include leukemias. It must be understood, however, that these lists are not meant to be complete, and that the prior art is aware of many other tumors that have β-glucuronidase and tyrosinase activity. However, whether or not the art is presently aware that any given tumor has β-glucuronidase or tyrosinase activity, this can be determined by any of the various methods of diagnosis discussed in the present specification. If it is determined that the tumor does indeed have both β-glucuronidase and tyrosinase activity, the therapeutic treatment of the present invention can be effectively used.

When it is desired to induce hyperthermia to increase β-glucuronidase activity, a method should be selected by which the temperature is raised as much as possible without risking damage to healthy portions of the body, such as the eyes. An increase of about 2° C. for whole body hyperthermia and as much as 4.5° C. for local hyperthermia is preferred. The hyperthermia should be timed to last about an hour at the time of greatest glucuronide concentration at the tumor site. For example, when local microwave treatment is selected, it should begin about one half hour after commencement of the intravenous conjugate drip and be continued for about one hour. The proper dosage of known pyrogens to achieve the desired degree of hyperthermia would be known to those skilled in the art, or could be easily empirically determined. A dosage of about 30 mg/day of dinitrophenol, for example, would be appropriate.

Because the triacetylated form of the conjugate is not affected by β-glucuronidase in the digestive tract, this form of the conjugate can be administered orally without loss of activity. Moreover, it has been found that, because the triacetylated form of the conjugate is lipid-soluble, it is retained in the body for a much longer time than the free acid form of the conjugate. The triacetylated form of the conjugate provides one additional level of protection for normal cells, as the phenolic compounds is not released in the body until the acetyl groups are removed and the glucuronic acid is removed from the phenolic compound. Primitive cells can produce acetylase along with a great variety of other enzymes, and this acetylase removes the acetyl groups from the conjugate. The more anaplastic (more immature) the tumor cells, the more enzymes they produce, so that the triacetylated form of the drug is more selectively toxic to tumor cells than even the conjugated form. Thus, since two steps are required to liberate the phenolic compound, the conjugates are even more preferentially delivered to the site of an active tumor than are the acid form of the conjugates.

When estrogen or testosterone are to be administered, a dosage of 5-15 mg/body weight/day would provide the desired inducement of β-glucuronidase activity.

To treat patients suffering from cancers which exhibit tyrosinase activity, the phenolic compounds are administered in the form of acetylated glucuronic acid conjugates. Capsules are formulated, generally containing approximately 0.6 gram/capsule of active ingredient. Generally, five capsules three times daily, providing nine grams/day of active ingredient are administered. The patient's serum is measured after a loading dosage is administered of the compound to maintain a level of approximately 1 mM of compound in the serum.

As noted above, para-methoxy-phenyl glucuronide is the preferred compound for use according to the present invention. This compound is preferred because it is particularly non-toxic to the non-cancer cells. As with the other glucuronide compounds of the present invention, para-methoxy-phenyl glucuronide can be used in either the triacetylated form or in the free acid form.

In the first step after administering para-methoxy-phenyl glucuronide to a patient, this "prodrug" is hydrolyzed at the cancer site by β-glucuronidase to yield 4-hydroxyl anisole. This reaction takes place only at the cancer site because only there is the enzyme β-glucuronidase available to catalyze the reaction. The 4-hydroxy-anisole that is released is then available as a substrate for the second reaction, which is catalyzed by the enzyme tyrosinase. The tyrosinase oxidizes the 4-hydroxy-anisole to methoxy-ortho-benzoquinone. The methoxy-ortho-benzoquinone is an unstable molecule that spontaneously releases hydrogen peroxide. When the hydrogen peroxide reaches a certain concentration, living membranes can no longer cope with the oxidative damage produced thereby, and are destroyed. To enhance the oxidative damage in these cancerous cells, the hydrogen peroxide concentration is further increased by inhibiting the reducing enzyme glutathione reductase.

The para-methoxy-phenyl glucuronide is particularly important because this prodrug becomes extremely toxic after two sequential steps of activation and potentiation, and concomitant inhibition of a third enzyme, glutathione reductase. This occurs via two sequential enzymatic systems that exist only at the malignant, growth, i.e., β-glucuronidase and tyrosinase.

By using any specific inhibitor of glutathione reductase, we were able to increase the damage that was inflicted on the cancerous cells by para-methoxy-phenyl glucuronide. The most promising, least toxic inhibitors of glutathione reductase are based upon the anti-malaria drug chloroquine. Of these compounds, chloroquine diphosphate is particularly useful. However, other compounds that can inhibit glutathione reductase include quinine or quinidine, quinine acetylsalicylate, quinine benzoate, quinine bisalicyloylsalicylate, quinine bisulfate, quinine carbonate, quinine dihydroiodide, quinine dihydrobromide, quinine dihydrochloride, quinine ethylcarbonate, quinine ethyl sulfate, quinine formate, quinine gluconate, quinine glycerophosphate, quinine hydroiodide, quinine hydrobromide, quinine hydrochloride, quinine hypophosphate, quinine lactate, quinine phenolsulfonate, quinine salicylate, quinine sulfate, quinine tannate, and quinine urea hydrochloride.

Other inhibitions of glutathione reductase that can be used include iodo-acetamide and cormastine, which is an anti-cancer drug itself, nifulidone which is an antibiotic, and its derivatives, can also be used to inhibit the activity of glutathione reductase.

Because para-methoxy-phenyl glucuronide is a glucuronide, it is hydrolyzed by the β-glucuronidase produced by the tumor cells to release 4-hydroxy anisole at the site of the tumor. The pH for optimal enzymatic activity for β-glucuronidase is 5.5, so that acidification of the tumor is desirable. This acidification of the tumor, as described elsewhere in this specification, can be achieved by administering glucose to the patient thirty minutes prior to the treatment, as orally administered glucose expressed itself in acidification of the tumor due to accumulation of lactic acid.

In a preferred treatment protocol, the patient is preferably on maintenance dosage of a corticosteroid, such as 4 mg of dexamethasone, throughout the duration of the treatment. This dosage ensures delay in premature fibrotic changes and interference with the blood and drug supply to the tumor. Of course, any of the conventional corticosteroids can be used for this purpose.

It should also be noted that corticosteroids inhibit the production of tumor necrosis factor, and thus reduce the malaise, loss of appetite, and cachexia that accompany malignant diseases. In addition, corticosteroids help in maintaining high levels of blood glucose, and for brain tumors, a higher dosage is useful. Omeprazole, Zantac, Cimetidine or other anti-ulcer drugs should also be administered concomitantly to prevent ulcers, since corticosteroids are known to induce ulcers.

EXAMPLE 1

A patient suffering from mammary intraductular poorly differentiated adenocarcinomas was treated with 5 capsules of 0.6 grams/capsule of triacetylated glucuronic acid conjugate of 4-hydroxyanisole. Tumors involved five conjoined axillary lymph nodes. The total tumor size was about 8×6×4 cm in the right breast. The dosage administered, once a level of 1 mM of triacetylated glucuronic acid conjugate of 4-hydroxyanisole in serum was attained, was five capsules of 0.6 grams active ingredient, administered orally three times a day.

Shortly after the first dose was administered, the patient experienced sever sharp pains at the locus of the tumor less than one hour after administration of the drug. The pain subsided after two hours, and soon thereafter the tumor was observed to shrink.

After three weeks of treatment, the total tumor size had shrunk to about 3×3×3 cm, and the skin surface above the tumor site that was red and excreted pus and had a cauliflower-like appearance became almost normal in appearance. After six weeks of treatment, the redness had disappeared and the cauliflower had shrunk almost completely; normal skin covered most of what had been the tumor area. The armpit lymph nodes had disappeared.

EXAMPLE 2

A patient suffering from mammary intraductular poorly differentiated adenocarcinoma was treated as above. Within six weeks, the tumor had almost completely disappeared. No side effects were observed.

EXAMPLE 3

A patient with malignant melanoma which had metastasized to the brain was near death. Capsules containing 0.6 gram of triacetylated glucuronic acid conjugate of 4-hydroxyanisole were administered to the patient to bring the serum concentration of the active ingredient to 1 mM, and then treatment was continued at a level of five 0.6 gram capsules, three times daily. After five months of therapy, MRI examination showed considerable shrinkage of the brain tumor, and the patient appears to be recovering fully.

EXAMPLE 4

A patient with lung cancer had the lung tumor removed surgically. Two months after surgery, the patient suffered loss of balance and equilibrium, accompanied by epileptic-like seizures. MRI examination revealed a tumor encompassing ¼ of the occipital area of the brain. Capsules containing 0.6 gram of triacetylated glucuronic acid conjugate of 4-hydroxyanisole were administered to the patient to bring the serum concentration of the active ingredient to 1 mM, and then treatment was continued at a level of five 0.6 gram capsules, three times daily. After two months of treatment, the patient exhibited no more symptoms, and had returned to work.

Examples 3 and 4, which describe the treatment of brain tumors, demonstrate that the triacetylated form of the phenolic-glucuronide conjugate are able to cross the blood-brain barrier to reach the tumor site.

EXAMPLE 5

Patients suffering from cancers having both glucuronidase and tyrosinase activity are treated by oral administration triocetylated of PMPG three times a day for seven days. Vitamin E is administered once daily while the patient is undergoing treatment because the vitamin E keeps tyrosinase in its reduced form, which is its active form during the treatment regimen, which generally lasts from about one to six weeks, depending upon the size of the tumor treated and the tumor's responce to treatment a quinine compound is administered once a week. The quinine compound, such as chlorquine diphosphate, is administered in amounts ranging from about 100 to about 1000 mg. Additionally, a corticosteroid, such as dexamethasone is administered in order to maintain high blood glucose levels. For brain tumors, a dosage of about 5-10 mg/day is administered; for other types of tumors, a dose of about 1-8 mg/day is sufficient.

Additionally, Moeprazole, Zantac or Cimetidine should be administered once or twice daily to prevent development of ulcers.

During therapy according to the present invention, no vitamin C supplementation or any ascorbate should be administered to the patient. Ascorbates, being antioxidants, protect the malignant cells from the oxidative damage caused by the metabolites of 4-hydroxy anisole. The vitamin E administered reduces the tyrosinase, in this case the vitamin E acts as a prooxidant.

The conjugates of the present invention can be administered to patients suffering from tyrosinase-dependent cancers at doses ranging from about 1-15 grams/day of total dosage. Although it has been found that maintaining a serum level of about 1 mM of conjugate is desirable, serum levels ranging from about 0.1 mM to about 10 mM can be used, depending upon the patient's response to the treatment.

The conjugates of the present invention can be combined with a pharmaceutically acceptable carrier therefore, and optionally other therapeutic and/or prophylactic ingredients. The carriers must be "acceptable" in the sense of being compatible with the other ingredients of the formulation and not deleterious to the recipient thereof.

Pharmaceutical formulations suitable for oral administration wherein the carrier is a solid are most preferably presented as unit dose formulations such as boluses, capsules, and the like, as well as sachets or tablets each containing a predetermined amount of the active ingredient. A tablet may be made by compression or molding, optionally with one or more accessory ingredients. Compressed tablets may be prepared by compressing in a suitable machine the active conjugate in a free-flowing form, such as a powder or granules optionally mixed with a binder, lubricant, interdiluent, lubricating, surface active or dispersing agent. Molded tablets may be made by molding the active conjugate with an inert liquid diluent. Tablets may be optionally coated and, if uncoated, may optionally be scored. Capsules may be prepared by filling the active conjugate, either alone or in admixture with one or more accessory ingredients, into the capsule cases and then sealing them in the usual manner. Cachets are analogous to capsules wherein the active conjugate together with any optional accessory ingredient is sealed in a rice paper envelope.

Pharmaceutical formulations suitable for oral administration in which the carrier is a liquid may conveniently be presented as a solution in an aqueous liquid or a non-aqueous liquid, or an an oil-in-water or water-in-oil liquid emulsion.

Pharmaceutical formulations suitable for parenteral administration are conveniently presented in unit does or multi-dose container which are sealed after introduction of the formulation until required for use.

It should be understood that in addition to the aforementioned carrier ingredients the pharmaceutical formulations described above may include, as appropriate, one or more additional carrier ingredients such as diluents, buffers, flavoring agents, binders, surface active agents, thickeners, lubricants, preservative (including anti-oxidants) and the like, and substances included for the purpose of rendering the formulation isotonic with the blood of the intended recipient.

The pharmaceutical formulations may be any formulation in which the active compound may be administered and include those suitable for oral or parenteral (including intramuscular and intravenous) administration. The formulations may, where appropriate, be conveniently presented in discrete dosage units and may be prepared by any of the methods well known in the art of pharmacy. All of the methods include the step of brining into association the active compound with liquid carriers or finely divided solid carriers of both and then, if necessary, shaping the product into the desired formulation.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method for selectively treating tumor cells which have both $\beta$-glucuronidase and tyrosinase activity comprising administering to a patient suffering from said tumor cells an effective amount to destroy said tumor cells of a conjugate made by conjugating glucuronic acid or a pharmaceutically acceptable ester or salt thereof to a cytotoxic phenolic compound which is also a substrate for tyrosinase.

2. The method according to claim 1 wherein the conjugate is formed from the triacetylated form of glucuronic acid.

3. The method according to claim 2 wherein the conjugate is administered orally.

4. The method according to claim 1 wherein the cytotoxic compound is selected from the group consisting of 4-hydroxyanisole, L-3,4-dihydroxyphenylalanine, dopamine, tert-butylcatechol, hydroquinone, 6-hydroxydopa, 4-tert-butyl phenol, 4-tert-amyl phenol, 4-benzomethoxy phenol and methyl gallate.

5. The method according to claim 4 wherein the cytotoxic compound is 4-hydroxyanisole.

6. The method according to claim 5 further comprising administering to said patient an effective amount of a compound that inhibits the activity of glutathione reductase.

7. The method according to claim 6 wherein said compound that inhibits the activity of glutathione reductase is selected from the group consisting of chloroquine diphosphate, quinine, quinidine, quinine acetylsalicylate, quinine benzoate, quinine bisalicyloylsalicylate, quinine bisulfate, quinine carbonate, quinine dihydroiodide, quinine dihydrobromide, quinine dihydrochloride, quinine ethylcarbonate, quinine ethyl sulfate, quinine formate, quinine gluconate, quinine glycerophosphate, quinine hydroiodide, quinine hydrobromide, quinine hydrochloride, quinine hypophosphate, quinine lactate, quinine phenolsulfonate, quinine salicylate, quinine sulfate, quinine tannate, iodo-acetamide, nifulidone, derivatives of nifulidone, carmustine and quinine urea hydrochloride.

8. The method according to claim 6 further comprising administering to said patient an effective amount of a corticosteroid to maintain high levels of glucose in the blood above about 180% of normal glucose levels in the blood.

9. The method according to claim 2 wherein the cytotoxic compound is selected from the group consisting of 4-hydroxyanisole, L-3,4-dihydroxyphenylalanine, dopamine, tert-butylcatechol, hydroquinone, 6-hydroxydopa, and methyl gallate.

10. The method according to claim 9 wherein the cytotoxic compound is 4-hydroxyanisole.

11. The method according to claim 1 wherein, prior to administration of said conjugate, the patient is administered an alkalinizing agent in an amount sufficient to maintain the pH level of the non-tumor tissues of the patient at approximately 7.4 during the treatment with said conjugate.

12. The method according to claim 1 wherein, prior to administering said conjugate, the tumor cells are hyperacidified.

13. The method according to claim 1 further including the step of inducing hyperthermia at least at the site of the tumor being treated to an extent sufficient to increase substantially the $\beta$-glucuronidase activity at the site without substantially affecting the overall health of the patient at the time of maximum conjugate concentration at the tumor site.

14. The method according to claim 11 wherein said hyperthermia is induced locally at the tumor by administration of the glucuronide of a pyrogen, by microwave treatment or by passage of electrical current through the body.

15. The method according to claim 1 further including the step of administering estrogen or testosterone substantially simultaneously with administration of said conjugate, wherein the tumor is not estrogen- or testosterone-dependent.

16. A composition for selectively treating tumor cells which have both β-glucuronidase activity and tyrosinase activity comprising an effective amount of a conjugate made by conjugating a glucuronide compound selected from the group consisting of glucuronic acid and pharmaceutically acceptable esters and salts thereof to a cytotoxic phenolic compound which is also a substrate for tyrosinase, and a pharmaceutically acceptable carrier.

17. The composition according to claim 16 wherein the glucuronide compound is a triacetylated glucuronic acid.

18. The composition according to claim 17 wherein the glucuronide compound is methyl (tri-O-acetyl-α-D-glucopyranosyl) bromide uronate.

19. The composition according to claim 16 wherein the cytotoxic phenolic compound is selected from the group consisting of 4-hydroxyanisole, tyrosine, L-3,4-dihydroxyphenylalanine, dopamine, tert-butylcatechol, hydroquinone, 6-hydroxydopa, and methyl gallate.

20. The composition according to claim 19 wherein the cytotoxic compound is 4-hydroxyanisole.

21. The composition according to claim 16 further comprising an effective amount of a quinine compound that inhibits the activity of glutathione reductase.

22. The composition according to claim 21 wherein said compound that inhibits the activity of gluthathione reductase is selected from the group consisting of chloroquine diphosphate, quinine, quinidine, quinine acetylsalicylate, quinine benzoate, quinine bisalicyloylsalicylate, quinine bisulfate, quinine carbonate, quinine dihydroiodide, quinine dihydrobromide, quinine dihydrochloride, quinine ethylcarbonate, quinine ethyl sulfate, quinine formate, quinine gluconate, quinine glycerophosphate, quinine hydroiodide, quinine hydrobromide, quinine hydrochloride, quinine hypophosphate, quinine lactate, quinine phenolsulfonate, quinine salicylate, quinine sulfate, quinine tannate, iodo-acetamide, nilfulidone, derivatives of nilfulidone, carmustine and quinine urea hydrochloride.

23. The composition according to claim 16 further comprising an effective amount of a corticosteroid to maintain high levels of glucose above 180% in the blood.

24. The composition according to claim 16 wherein the carrier is suitable for parenteral administration.

25. The composition according to claim 17 wherein the composition is suitable for oral administration.

26. The method according to claim 1 wherein the tumor cells are selected from the group consisting of solid breast tumors, lung carcinoma, colon carcinoma, testicular carcinoma, hepatic carcinoma, pancreatic carcinoma, ovarian carcinoma, bronchogenic carcinoma, prostate carcinmoa, Hodgkin's disease, and rectal carcinoma.

27. The method according to claim 26 wherein the tumor cells are solid breast tumors.

* * * * *